United States Patent
Yuzawa

(10) Patent No.: US 12,327,626 B2
(45) Date of Patent: Jun. 10, 2025

(54) DIAGNOSIS SUPPORT DEVICE, DIAGNOSIS SUPPORT METHOD, AND DIAGNOSIS SUPPORT PROGRAM

(71) Applicant: FUJIFILM Corporation, Tokyo (JP)

(72) Inventor: Takuya Yuzawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 400 days.

(21) Appl. No.: 17/749,108

(22) Filed: May 19, 2022

(65) Prior Publication Data
US 2022/0277837 A1 Sep. 1, 2022

Related U.S. Application Data

(63) Continuation of application No. PCT/JP2020/044683, filed on Dec. 1, 2020.

(30) Foreign Application Priority Data

Dec. 17, 2019 (JP) .................. 2019-227017

(51) Int. Cl.
- G16H 30/40 (2018.01)
- G06T 7/00 (2017.01)
- G16H 50/20 (2018.01)

(52) U.S. Cl.
CPC ........... G16H 30/40 (2018.01); G06T 7/0014 (2013.01); G16H 50/20 (2018.01); *G06T 2207/20081* (2013.01); *G06T 2207/30096* (2013.01)

(58) Field of Classification Search
CPC ...... G16H 30/40; G16H 50/20; G06T 7/0014; G06T 2207/20081; G06T 2207/30096

See application file for complete search history.

(56) References Cited

U.S. PATENT DOCUMENTS

| | | | |
|---|---|---|---|
| 9,201,902 B2 | 12/2015 | Doi et al. | |
| 9,798,770 B2 | 10/2017 | Ohashi et al. | |
| 11,010,375 B2 | 5/2021 | Ohashi et al. | |
| 2009/0310836 A1 | 12/2009 | Krishnan et al. | |

(Continued)

FOREIGN PATENT DOCUMENTS

| | | |
|---|---|---|
| CN | 102426583 | 4/2012 |
| JP | 2011008374 | 1/2011 |

(Continued)

OTHER PUBLICATIONS

"International Search Report (Form PCT/ISA/210) of PCT/JP2020/044683," mailed on Feb. 22, 2021, with English translation thereof, pp. 1-7.

(Continued)

*Primary Examiner* — John R Wallace

(74) *Attorney, Agent, or Firm* — JCIPRNET

(57) ABSTRACT

A diagnosis support device receives an input retrieval word, retrieves, from a plurality of medical images, each including a lesion region and associated with a key finding that is a key to specify a diagnosis name of the lesion region, a medical image associated with a key finding corresponding to the retrieval word, classifies a retrieved medical image group according to a degree of similarity of images, and detects a lesion candidate region in an examination image on the basis of the degree of similarity between the examination image and a classification result.

6 Claims, 4 Drawing Sheets

(56) References Cited

U.S. PATENT DOCUMENTS

2010/0293164 A1* 11/2010 Weese ................ G06F 16/5866
707/E17.014
2012/0283574 A1   11/2012 Park et al.
2020/0327979 A1* 10/2020 Ishii ....................... G16H 30/40

FOREIGN PATENT DOCUMENTS

| JP | 2013152701 | 8/2013 |
| JP | 2014127011 | 7/2014 |
| JP | 2015203920 | 11/2015 |
| WO | 2013088806 | 6/2013 |

OTHER PUBLICATIONS

"Written Opinion of the International Searching Authority (Form PCT/ISA/237)" of PCT/JP2020/044683, mailed on Feb. 22, 2021, with English translation thereof, pp. 1-6.
Office Action of Japan Counterpart Application, with English translation thereof, issued on Jun. 6, 2023, pp. 1-5.

\* cited by examiner

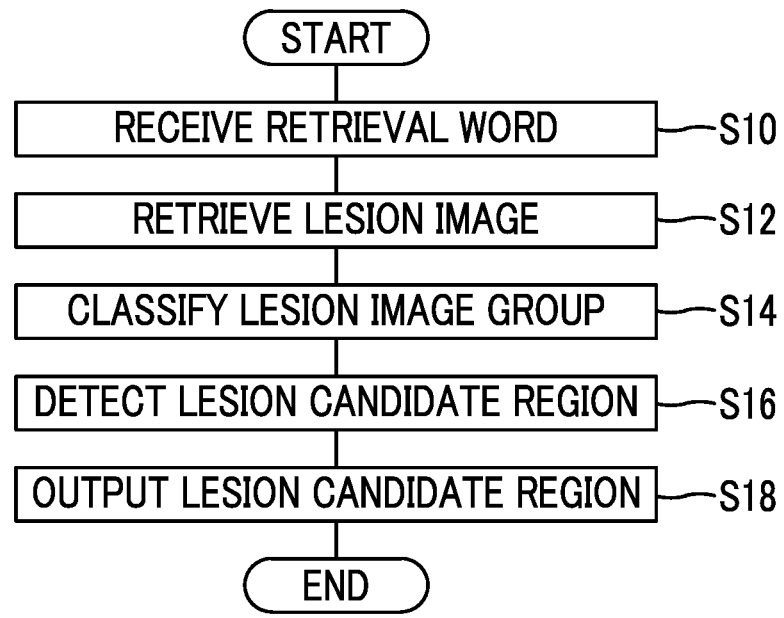
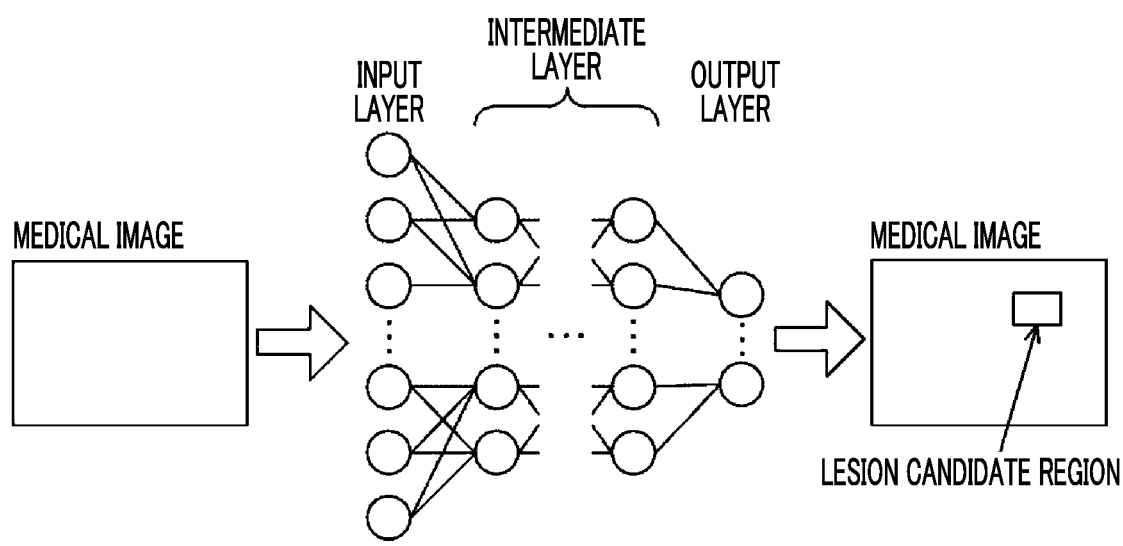

DIAGNOSIS SUPPORT DEVICE, DIAGNOSIS SUPPORT METHOD, AND DIAGNOSIS SUPPORT PROGRAM

CROSS-REFERENCE TO RELATED APPLICATIONS

This application is a Continuation of PCT International Application No. PCT/JP2020/044683 filed on Dec. 1, 2020, which claims priority under 35 U.S.C § 119(a) to Japanese Patent Application No. 2019-227017 filed on Dec. 17, 2019. Each of the above application(s) is hereby expressly incorporated by reference, in its entirety, into the present application.

BACKGROUND OF THE INVENTION

1. Field of the Invention

The present disclosure relates to a diagnosis support device, a diagnosis support method, and a non-transitory computer readable recording medium storing a diagnosis support program.

2. Description of the Related Art

A similar case retrieval system that acquires and presents a case similar to a retrieval input case including a medical document via retrieval from among retrieval target cases including medical documents is disclosed (see JP2015-203920A). This similar case retrieval system acquires, via retrieval, a case having a feature amount in which a degree of similarity with respect to the feature amount of the retrieval input case is higher than a predetermined value, from among the retrieval target cases.

SUMMARY OF THE INVENTION

Meanwhile, in recent years, there has been proposed a method of detecting a lesion candidate region from a medical image using a trained model obtained by machine learning such as deep learning. However, with this method, it is difficult to detect a lesion candidate region in which machine learning is not performed. In addition, a large number of case images are required for machine learning, and it is difficult to detect various lesion candidate regions in a general-purpose manner.

In the technique disclosed in JP2015-203920A, a case having a degree of similarity higher than a predetermined value with respect to the feature amount of the retrieval input case including the medical document is retrieved. Therefore, even with this technique, it may not be possible to detect various lesion candidate regions in a general-purpose manner.

The present disclosure has been made in view of the above circumstances, and provides a diagnosis support device, a diagnosis support method, and a non-transitory computer readable recording medium storing a diagnosis support program capable of detecting various lesion candidate regions in a general-purpose manner.

There is provided a diagnosis support device of the present disclosure comprising: at least one processor, in which the processor receives an input retrieval word, retrieves, from a plurality of medical images, each including a lesion region and associated with a key finding that is a key to specify a diagnosis name of the lesion region, a medical image associated with a key finding corresponding to the retrieval word, classifies a retrieved medical image group according to a degree of similarity of images, and detects a lesion candidate region in an examination image on the basis of the degree of similarity between the examination image and a classification result.

In the diagnosis support device of the present disclosure, the processor may receive a plurality of the retrieval words, and retrieve, from the plurality of medical images, a medical image associated with the key finding corresponding to all or any of the plurality of retrieval words.

Further, in the diagnosis support device of the present disclosure, the processor may detect the lesion candidate region in the examination image on the basis of the degree of similarity between the examination image and a representative image of the classified images.

Further, in the diagnosis support device of the present disclosure, in a case where there is a trained model that is trained in advance to receive a medical image as an input and to output a lesion candidate region in the input medical image and that is associated with the key finding corresponding to the retrieval word, the processor may detect the lesion candidate region in the examination image on the basis of the examination image and the trained model.

Further, in the diagnosis support device of the present disclosure, the processor may detect, as the lesion candidate region in the examination image, a region in which the degree of similarity is a first threshold value or more in the examination image, and change the first threshold value to a value larger than an immediately preceding value in a case where the number of the detected lesion candidate regions is a second threshold value or more, and detect the lesion candidate region in the examination image again.

Further, there is provided a diagnosis support method of the present disclosure that is executed by a processor provided in a diagnosis support device, the diagnosis support method comprising: receiving an input retrieval word; retrieving, from a plurality of medical images, each including a lesion region and associated with a key finding that is a key to specify a diagnosis name of the lesion region, a medical image associated with a key finding corresponding to the retrieval word; classifying a retrieved medical image group according to a degree of similarity of images; and detecting a lesion candidate region in an examination image on the basis of the degree of similarity between the examination image and a classification result.

Further, there is provided a non-transitory computer readable recording medium storing a diagnosis support program of the present disclosure for causing a processor provided in a diagnosis support device to execute a process comprising: receiving an input retrieval word; retrieving, from a plurality of medical images, each including a lesion region and associated with a key finding that is a key to specify a diagnosis name of the lesion region, a medical image associated with a key finding corresponding to the retrieval word; classifying a retrieved medical image group according to a degree of similarity of images; and detecting a lesion candidate region in an examination image on the basis of the degree of similarity between the examination image and a classification result.

According to the present disclosure, it is possible to detect various lesion candidate regions in a general-purpose manner.

BRIEF DESCRIPTION OF THE DRAWINGS

FIG. 7 is a flowchart showing an example of lesion candidate region detection processing.

FIG. 8 is a diagram showing an example of a trained model.

DESCRIPTION OF THE PREFERRED EMBODIMENTS

Hereinafter, an exemplary embodiment of the technique of the present disclosure will be described in detail with reference to the drawings.

Figure 1:
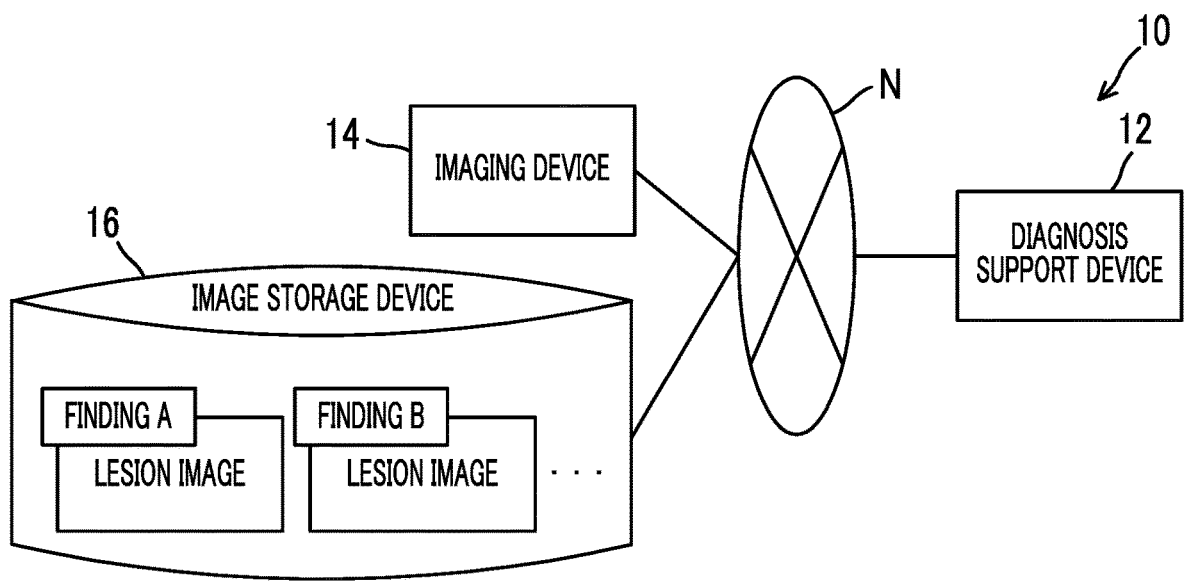
FIG. 1 is a block diagram showing an example of a configuration of a diagnosis support system.

First, the configuration of a diagnosis support system 10 according to the present embodiment will be described with reference to FIG. 1. As shown in FIG. 1, the diagnosis support system 10 includes a diagnosis support device 12, an imaging device 14, and an image storage device 16. The diagnosis support device 12, the imaging device 14, and the image storage device 16 are each connected to a network N and can communicate with each other through the network N.

The imaging device 14 is a device that generates a medical image representing a part to be diagnosed of a subject to be examined by imaging the part. Examples of the imaging device 14 include an imaging device that captures a radiographic image, and an imaging device that captures a three-dimensional image formed of a plurality of tomographic images. Examples of the imaging device that captures the three-dimensional image include a computed tomography (CT) device, a magnetic resonance imaging (Mill) device, and a positron emission tomography (PET) device.

Figure 2:
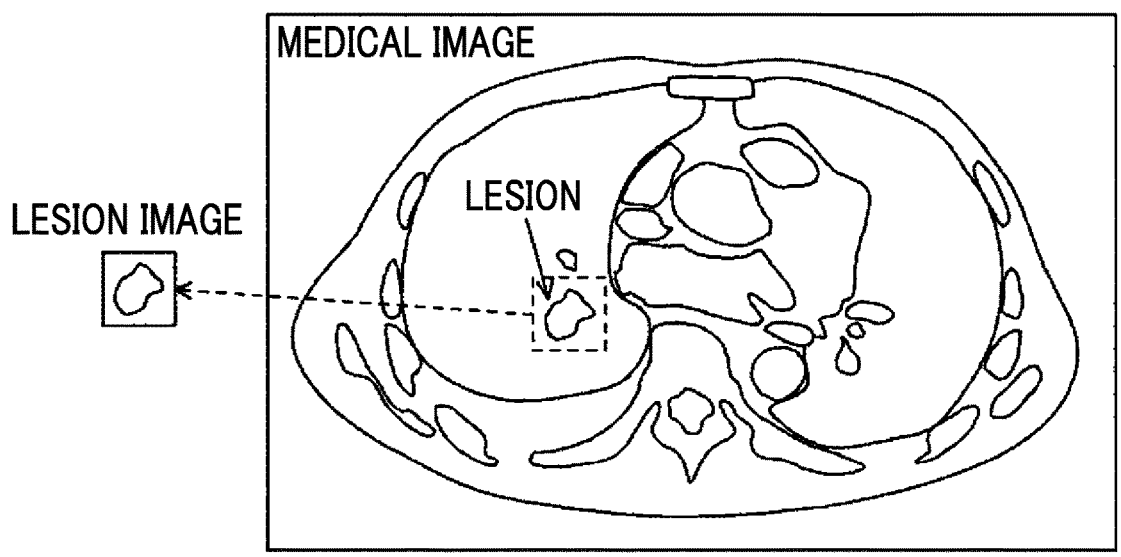
FIG. 2 is a view illustrating a lesion image.

The image storage device 16 is a computer that stores and manages medical images, and comprises, for example, a storage device that stores medical images. The image storage device 16 according to the present embodiment stores a plurality of medical images (hereinafter, referred to as "lesion images"), each including a lesion region. As shown in FIG. 2, the lesion image according to the present embodiment is an image obtained by cutting out a part of the medical image including the lesion region from the medical image generated by the imaging device 14.

Further, as shown in FIG. 1, the lesion image according to the present embodiment is associated with a key finding that is a key to specify a diagnosis name of the lesion region. A key finding means a characteristic finding in specifying the diagnosis name of the lesion region. In addition, the plurality of lesion images stored in the image storage device 16 include various lesion images regardless of the location of an organ, such as a right lung or a left lung, an image type, such as a CT image or an MM image, and the degree of progression of the lesion, such as stage 1 or stage 2, and the like. The generation of the lesion image and the association of the key finding with the lesion image are performed in advance by a user of the diagnosis support system 10.

The image storage device 16 transmits/receives the medical images generated by the imaging device 14 between the diagnosis support device 12 and the imaging device 14 through the network N. The storage format of the medical image and the communication between devices through the network N are based on a protocol, such as digital imaging and communications in medicine (DICOM). The lesion image and the key finding may be stored in a storage unit 22 of the diagnosis support device 12, which will be described later.

Next, a hardware configuration of the diagnosis support device 12 according to the present embodiment will be described with reference to FIG. 3. Examples of the diagnosis support device 12 include a personal computer and a server computer. The diagnosis support device 12 may be a cloud server.

Figure 3:
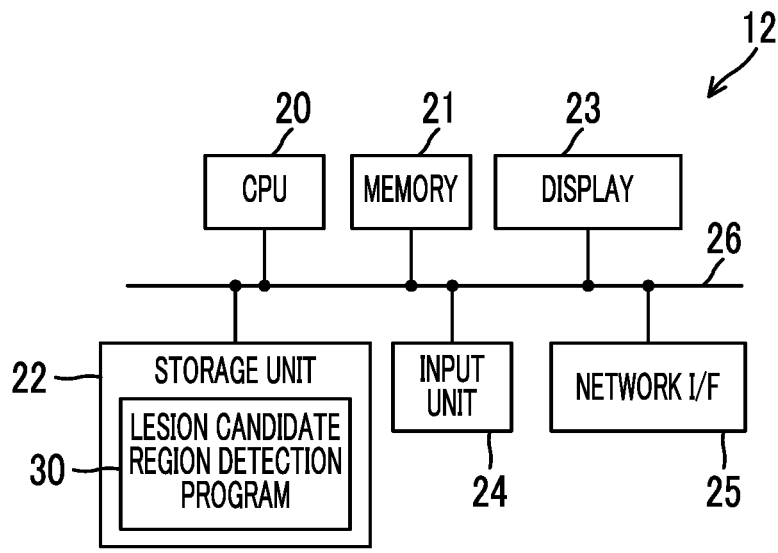
FIG. 3 is a block diagram showing an example of a hardware configuration of a diagnosis support device.

As shown in FIG. 3, the diagnosis support device 12 includes a central processing unit (CPU) 20, a memory 21 as a temporary storage area, and the nonvolatile storage unit 22. The diagnosis support device 12 includes a display 23, such as a liquid crystal display, an input unit 24, such as a keyboard and a mouse, and a network interface (I/F) 25 connected to the network N. The CPU 20, the memory 21, the storage unit 22, the display 23, the input unit 24, and the network I/F 25 are connected to a bus 26.

The storage unit 22 is realized by a hard disk drive (HDD), a solid state drive (SSD), a flash memory, or the like. The storage unit 22 as a storage medium stores a lesion candidate region detection program 30. The CPU 20 reads the lesion candidate region detection program 30 from the storage unit 22, loads the lesion candidate region detection program 30 into the memory 21, and executes the loaded lesion candidate region detection program 30.

Figure 4:
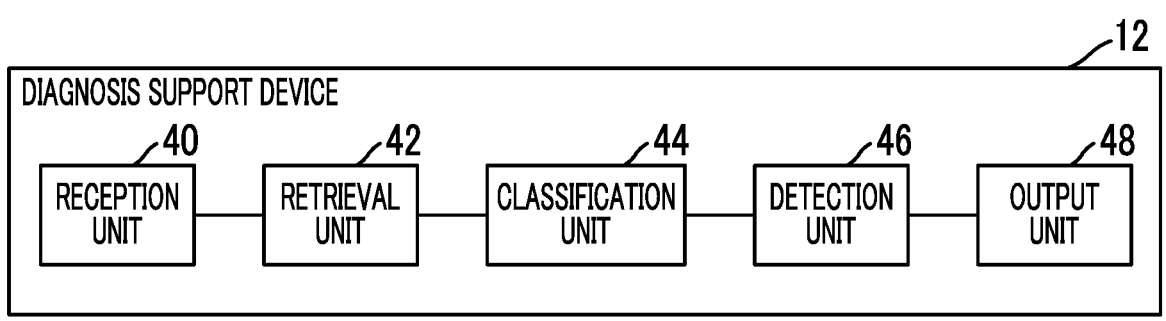
FIG. 4 is a block diagram showing an example of a functional configuration of the diagnosis support device.

Next, the functional configuration of the diagnosis support device 12 according to the present embodiment will be described with reference to FIG. 4. As shown in FIG. 4, the diagnosis support device 12 includes a reception unit 40, a retrieval unit 42, a classification unit 44, a detection unit 46, and an output unit 48. The CPU 20 executes the lesion candidate region detection program 30 to function as the reception unit 40, the retrieval unit 42, the classification unit 44, the detection unit 46, and the output unit 48.

The user inputs a retrieval word for retrieving a lesion candidate region that the user wants to detect in an examination image obtained by imaging the subject to be examined of a diagnosis target via the imaging device 14, through the input unit 24. The reception unit 40 receives the retrieval word input by the user through the input unit 24. For example, in a case where the examination image is an image obtained by imaging the lung of the subject to be examined and the user wants to know whether or not the examination image includes metastatic lung cancer, the user inputs a retrieval word, such as "metastatic lung cancer". The retrieval word is not limited to one word, and may be a plurality of words, for example, "lung cancer, metastatic".

Figure 5:
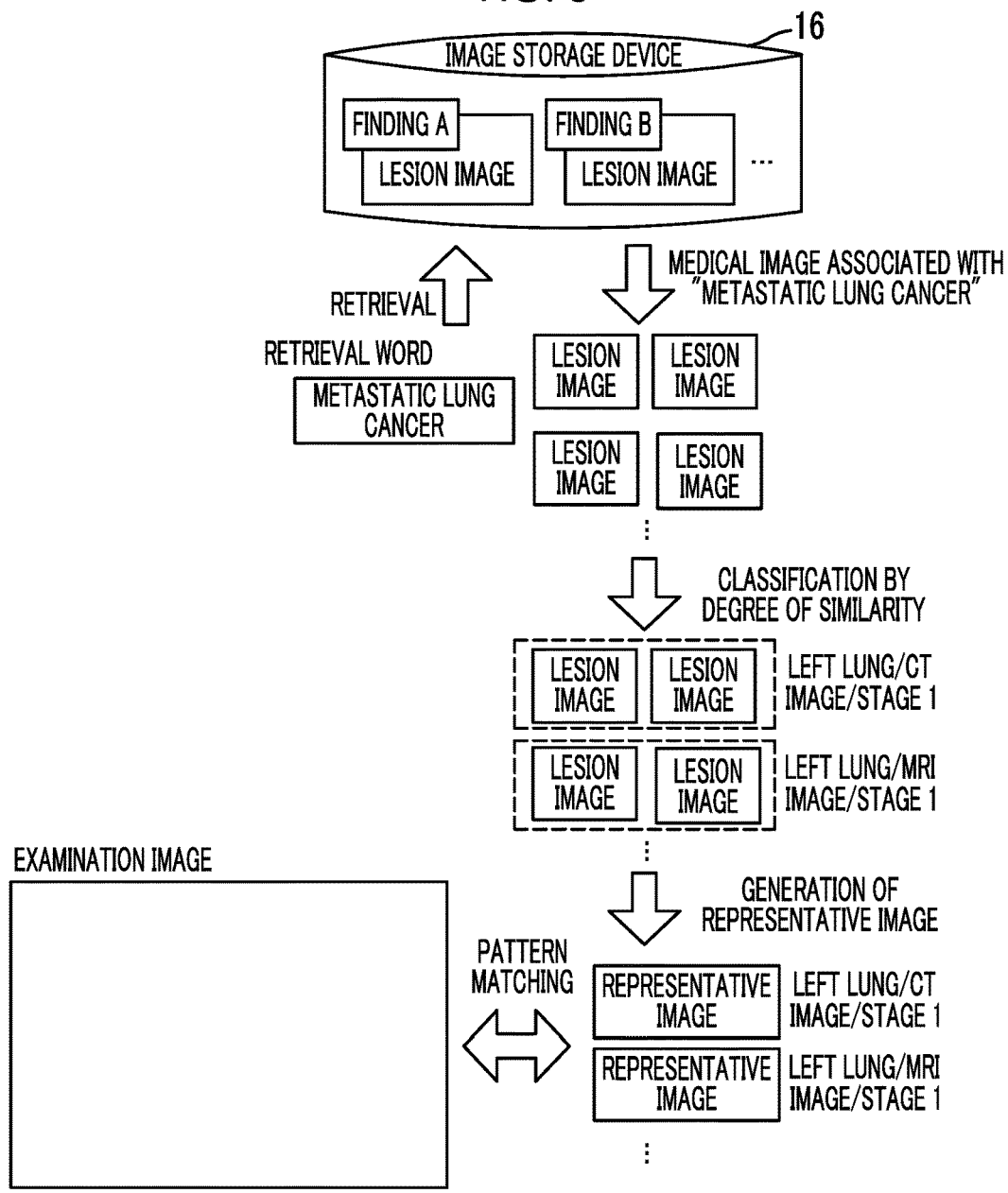
FIG. 5 is a diagram illustrating detection processing of a lesion candidate region.

As shown in FIG. 5, the retrieval unit 42 retrieves lesion images associated with the key finding corresponding to the retrieval word, which is received by the reception unit 40, from the plurality of lesion images stored in the image storage device 16. In a case where one retrieval word is received by the reception unit 40, the retrieval unit 42 retrieves the lesion images associated with the key finding corresponding to the one retrieval word. Alternatively, in a case where a plurality of retrieval words are received by the reception unit 40, the retrieval unit 42 retrieves the lesion images associated with the key finding corresponding to all or any of the plurality of retrieval words. Whether the retrieval unit 42 retrieves the lesion images associated with the key finding corresponding to all or any of the plurality of retrieval words can be designated by the user, for example, using a retrieval option.

The classification unit 44 classifies a lesion image group retrieved by the retrieval unit 42 according to the degree of similarity of images via a well-known method such as pattern matching. As shown in FIG. 5, the classification unit 44 classifies lesion images having the same organ location, image type, lesion progression degree, and the like into the same group. In the example of FIG. 5, a broken-line rectangle represents the group.

The detection unit 46 detects a lesion candidate region in the examination image on the basis of the degree of similarity between the examination image and the classification result performed by the classification unit 44. Specifically, as shown in FIG. 5, first, the detection unit 46 generates a representative image of the lesion image group for each group classified by the classification unit 44. Examples of the representative image include an average image in which each pixel value is an average value of the pixel values of the respective pixels of all the lesion images in the lesion image group. The representative image is not limited to the average image as long as the representative image is an image representing the lesion image group of the group. For example, each pixel value of the representative image may be a median value of the pixel values of the respective pixels of all the images in the lesion image group.

Next, as shown in FIG. 5, the detection unit 46 derives the degree of similarity to each representative image, for each partial region having the same size as the representative image in the examination image. For example, a well-known method such as pattern matching can be used to derive the degree of similarity. Then, the detection unit 46 detects a partial region in which the derived degree of similarity is a predetermined threshold value or more, as the lesion candidate region. The threshold value, in this case, is determined, for example, according to the required detection accuracy of the lesion candidate region. For example, in a case where it is desired to detect a larger number of lesion candidate regions even with low accuracy, the threshold value is set to a smaller value than a case where it is desired to detect lesion candidate regions with high accuracy.

The detection unit 46 may detect, as the lesion candidate region, a partial region in which the derived degree of similarity is a first threshold value or more, and change the first threshold value to a value larger than an immediately preceding value in a case where the number of the detected lesion candidate regions is a second threshold value or more, and detect the lesion candidate region in the examination image again. That is, in a case where the number of detected lesion candidate regions is too large, the detection unit 46 considers that the lesion candidate regions with low accuracy are also detected, changes the first threshold value to a large value, and detects the lesion candidate region again. With this, it is possible to detect the lesion candidate region with appropriate accuracy.

Figure 6:
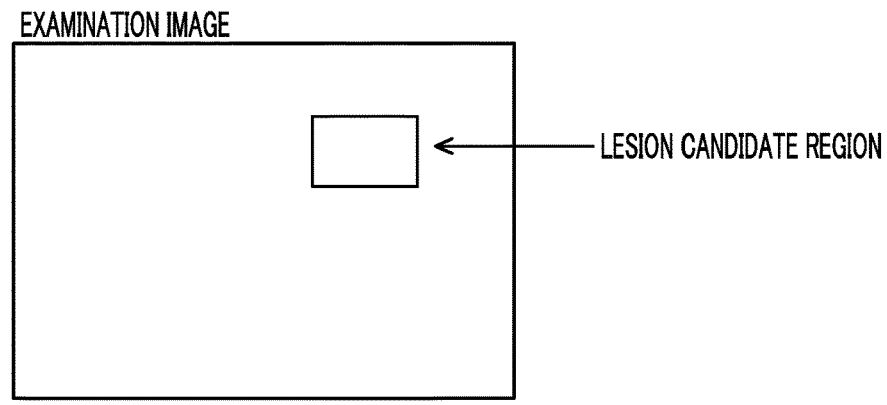
FIG. 6 is a view showing an example of the lesion candidate region detected from an examination image.

The output unit 48 outputs the examination image with the lesion candidate region, which is detected by the detection unit 46, superimposed thereon, to the display 23. With this, as shown in FIG. 6 as an example, the lesion candidate region corresponding to the retrieval word in the examination image is displayed on the display 23. The output unit 48 may output the lesion candidate region detected by the detection unit 46, to the storage unit 22. With this, the lesion candidate region in the examination image is stored in the storage unit 22.

Next, an operation of the diagnosis support device 12 according to the present embodiment will be described with reference to FIG. 7. The CPU 20 executes the lesion candidate region detection program 30, whereby lesion candidate region detection processing shown in FIG. 7 is executed. The lesion candidate region detection processing is executed, for example, in a case where a retrieval word and an execution instruction of the lesion candidate region detection processing are input by the user through the input unit 24.

In step S10 of FIG. 7, the reception unit 40 receives the retrieval word input by the user through the input unit 24. In step S12, as described above, the retrieval unit 42 retrieves the lesion images associated with the key finding corresponding to the retrieval word received in step S10, from the plurality of lesion images stored in the image storage device 16.

In step S14, as described above, the classification unit 44 classifies the lesion image group retrieved in step S12 according to the degree of similarity of images via a well-known method such as pattern matching. In step S16, as described above, the detection unit 46 detects the lesion candidate region in the examination image on the basis of the degree of similarity between the examination image and the classification result obtained by the processing in step S14. In step S18, as described above, the output unit 48 outputs the examination image with the lesion candidate region, which is detected in step S16, superimposed thereon, to the display 23. When the processing of step S18 ends, the lesion candidate region detection processing ends.

As described above, according to the present embodiment, the input retrieval word is received, and the lesion image associated with the key finding corresponding to the retrieval word is retrieved from the plurality of lesion images associated with the key finding that is a key to specify the diagnosis name of the lesion region. Then, the retrieved lesion image group is classified according to the degree of similarity of images, and the lesion candidate region in the examination image is detected on the basis of the degree of similarity between the examination image and the classification result. Accordingly, it is possible to detect the lesion candidate region even for a lesion for which a large amount of training data cannot be collected. In addition, it is possible to detect various lesion candidate regions in a general-purpose manner according to the free retrieval word input by the user.

In the above-described embodiment, for example, in a case where a large number of medical images, each including a specific lesion, has been collected, the storage unit 22 of the diagnosis support device 12 may store, in advance, a trained model generated by machine learning such as deep learning on the basis of the collected medical images. The trained model, in this case, is trained in advance to receive the medical image as an input and to output the lesion candidate region in the input medical image, thereby generating the trained model. Further, examples of the trained model, in this case, include a deep neural network model that receives the medical image as an input and outputs the lesion candidate region in the input medical image, as shown in FIG. 8 as an example. Such a trained model is generated by machine learning using an error backpropagation method or the like by preparing a large number of combinations of medical images and lesion candidate regions in medical images as training data. In addition, this trained model is associated with key finding that is a key to specify the diagnosis name of the lesion region detected by the trained model.

In this exemplary embodiment, the detection unit 46 detects the lesion candidate region in the examination image on the basis of the examination image and the trained model in a case where the storage unit 22 has the trained model associated with the key finding corresponding to the retrieval word, which is received by the reception unit 40. Specifically, the detection unit 46 detects the lesion candidate region in the examination image by acquiring the lesion candidate region in the examination image, which is output from the trained model in response to the input of the examination image to the trained model. With this, it is possible to accurately detect the lesion candidate region.

In the above-described embodiment, for example, the following various processors can be used as the hardware structures of processing units that execute various kinds of processing, such as the reception unit 40, the retrieval unit 42, the classification unit 44, the detection unit 46, and the output unit 48. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU, which is a general-purpose processor that executes software (programs) to function as various processing units, as described above.

One processing unit may be constituted of one of the various processors or may be constituted of a combination of two or more processors of the same type or different types (for example, a combination of a plurality of FPGAs and a combination of a CPU and an FPGA). Alternatively, the plurality of processing units may be constituted of one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and a server. A second example of the configuration is an aspect in which a processor that implements all of the functions of a system including the plurality of processing units with one integrated circuit (IC) chip is used. A representative example of the aspect is a system on chip (SoC). As described above, various processing units are constituted of one or more of the various processors as the hardware structures.

Furthermore, as the hardware structures of the various processors, more specifically, an electrical circuit (circuitry) in which circuit elements, such as semiconductor elements, are combined can be used.

In the above-described embodiment, the aspect in which the lesion candidate region detection program 30 is stored (installed) in the storage unit 22 in advance has been described, but the present disclosure is not limited thereto. The lesion candidate region detection program 30 may be provided in a form in which the lesion candidate region detection program 30 is recorded on a recording medium, such as a compact disc read only memory (CD-ROM), a digital versatile disc read only memory (DVD-ROM), and a Universal Serial Bus (USB) memory. Alternatively, the lesion candidate region detection program 30 may also be provided in a form in which the lesion candidate region detection program 30 is downloaded from an external device through the network.

EXPLANATION OF REFERENCES

10: diagnosis support system
12: diagnosis support device
14: imaging device
16: image storage device
20: CPU
21: memory
22: storage unit
23: display
24: input unit
25: network I/F
26: bus
30: lesion candidate region detection program
40: reception unit
42: retrieval unit
44: classification unit
46: detection unit
48: output unit
N: network

What is claimed is:

1. A diagnosis support device comprising:
at least one processor,
wherein the processor is configured to:
 receive an input retrieval word;
 retrieve, from a plurality of medical images, each including a lesion region and associated with a key finding that is a key to specify a diagnosis name of the lesion region, a medical image associated with a key finding corresponding to the retrieval word;
 classify a retrieved medical image group according to a degree of similarity of images; and
 detect a lesion candidate region in an examination image on the basis of the degree of similarity derived by using pattern matching between the examination image and a representative image of the classified medical image group, wherein the representative image of the classified medical image group is generated from the plurality of medical images including lesion region.

2. The diagnosis support device according to claim 1,
wherein the processor is configured to:
 receive a plurality of the retrieval words; and
 retrieve, from the plurality of medical images, a medical image associated with the key finding corresponding to all or any of the plurality of retrieval words.

3. The diagnosis support device according to claim 1,
wherein in a case where there is a trained model that is trained in advance to receive a medical image as an input and to output a lesion candidate region in the input medical image and that is associated with the key finding corresponding to the retrieval word,
the processor is configured to detect the lesion candidate region in the examination image on the basis of the examination image and the trained model.

4. The diagnosis support device according to claim 1,
wherein the processor is configured to detect, as the lesion candidate region in the examination image, a region in which the degree of similarity is a first threshold value or more in the examination image, and change the first threshold value to a value larger than an immediately preceding value in a case where the number of the detected lesion candidate regions is a second threshold value or more, and detect the lesion candidate region in the examination image again.

5. A diagnosis support method comprising:
receiving an input retrieval word;
retrieving, from a plurality of medical images, each including a lesion region and associated with a key finding that is a key to specify a diagnosis name of the lesion region, a medical image associated with a key finding corresponding to the retrieval word;

classifying a retrieved medical image group according to a degree of similarity of images; and detecting a lesion candidate region in an examination image on the basis of the degree of similarity derived by using pattern matching between the examination image and a representative image of the classified medical image group, wherein the representative image of the classified medical image group is generated from the plurality of medical images including lesion region.

6. A non-transitory computer readable recording medium storing a diagnosis support program for causing a computer to execute the diagnosis support method according to claim 5.

* * * * *